US008119350B2

(12) United States Patent
Chen et al.

(10) Patent No.: US 8,119,350 B2
(45) Date of Patent: Feb. 21, 2012

(54) METHOD OF SURFACE PLASMON RESONANCE (SPR) TO DETECT GENOMIC ABERRATIONS IN PATIENTS WITH MULTIPLE MYELOMA

(75) Inventors: Zhong Chen, Sandy, UT (US); Ning Liu, Beijing (CN)

(73) Assignee: CMED Technologies Ltd, Road Town, Tortola (VG)

( * ) Notice: Subject to any disclaimer, the term of this patent is extended or adjusted under 35 U.S.C. 154(b) by 423 days.

(21) Appl. No.: 12/441,710

(22) PCT Filed: Aug. 23, 2007

(86) PCT No.: PCT/US2007/076658
§ 371 (c)(1),
(2), (4) Date: Mar. 17, 2009

(87) PCT Pub. No.: WO2008/082710
PCT Pub. Date: Jul. 10, 2008

(65) Prior Publication Data
US 2009/0273787 A1 Nov. 5, 2009

Related U.S. Application Data

(60) Provisional application No. 60/826,859, filed on Sep. 25, 2006.

(51) Int. Cl.
C12Q 1/68 (2006.01)
G01N 33/551 (2006.01)
G01N 33/553 (2006.01)

(52) U.S. Cl. ......... 435/6.11; 385/12; 385/129; 385/130; 422/82.11; 435/288.7; 436/164; 436/524; 436/525; 436/805

(58) Field of Classification Search .................. None
See application file for complete search history.

(56) References Cited

U.S. PATENT DOCUMENTS

| | | | |
|---|---|---|---|
| 4,609,629 A | 9/1986 | Timpl | |
| 4,755,458 A | 7/1988 | Rabbani et al. | |
| 5,242,828 A | 9/1993 | Bergström et al. | |
| 5,478,755 A | 12/1995 | Attridge et al. | |
| 5,573,957 A | 11/1996 | Cardone et al. | |
| 5,629,213 A | 5/1997 | Kornguth et al. | |
| 5,712,087 A | 1/1998 | Houghton et al. | |
| 5,846,740 A | 12/1998 | Tobin et al. | |
| 6,197,515 B1 | 3/2001 | Bamdad et al. | |
| 6,468,657 B1 | 10/2002 | Hou et al. | |
| 6,534,281 B2 | 3/2003 | Kitajima et al. | |
| 6,627,397 B1 | 9/2003 | Nakamura et al. | |
| 6,726,881 B2 | 4/2004 | Shinoki et al. | |
| 6,809,196 B2 | 10/2004 | Bamdad et al. | |
| 6,956,651 B2 | 10/2005 | Lackritz et al. | |
| 6,967,074 B2 | 11/2005 | Duffy et al. | |
| 7,135,281 B2 | 11/2006 | Doorbar | |
| 2003/0032202 A1 | 2/2003 | Stolowitz et al. | |
| 2004/0115684 A1 | 6/2004 | Costa | |
| 2004/0219523 A1 | 11/2004 | Stanton et al. | |
| 2004/0234970 A1 | 11/2004 | Yoo | |
| 2005/0019933 A1 | 1/2005 | Andersson et al. | |
| 2005/0064450 A1 | 3/2005 | Lucas et al. | |
| 2005/0100974 A1 | 5/2005 | Duffy et al. | |
| 2005/0106562 A1 | 5/2005 | Abbott et al. | |
| 2005/0153357 A1 | 7/2005 | Eichler et al. | |
| 2006/0083858 A1 | 4/2006 | Barden et al. | |
| 2006/0211137 A1 | 9/2006 | Ezoe et al. | |

FOREIGN PATENT DOCUMENTS

| | | |
|---|---|---|
| WO | 01/68915 | 9/2001 |
| WO | 2004/081572 | 9/2004 |
| WO | 2005/017122 | 2/2005 |
| WO | 2006/074130 | 7/2006 |

OTHER PUBLICATIONS

Artsaenko et al., Abrogation of hepatitis C virus NS3 helicase enzymatic activity by recombinant human antibodies, Journal of General Virology, 2003, pp. 2323-2332, vol. 84.
Aslan et al., Tunable plasmonic glucose sensing based on the dissociation of Con A-aggregated dextran-coated gold colloids, Analytica Chimica Acta, 2004, pp. 139-144, vol. 517.
Breveglieri et al., Recent advances in molecular diagnosis using surface plastmon resonance and biosensor technology for detection of $-thalassemia mutations, Minerva Biotec, 2003, pp. 93-97, vol. 15.
Campagnolo et al., Real-Time, label-free monitoring of tumor antigen and serum antibody interactions, Journal of Biochemcial and Biophysical Methods, 2004, pp. 283-298, vol. 61.
Choi et al., Enhanced performance of a surface plasmon resonance immunosensor for detecting Ab-GAD antibody based on the modified self-assembled monolayers, Biosensors and Bioelectronics, 2005, pp. 378-383, vol. 21.
Engels et al., Comprehensive analysis of human subtelomeres with combined binary ration labelling fluorescence in situ hybridisation, European Journal of Human Genetics, 2003, pp. 643-651, vol. 11.
Hagedorn et al., Evaluation of INNO-LIA Syphilis Assay as a Confirmatory Test for Syphilis, Journal of Clinical Microbiology, Mar. 2002, pp. 973-978, vol. 40, No. 3.
Halling et al., Clinical Comparison of the Treponema pallidum CAPTIA Syphilis-G Enzyme Immunoassay with the Fluorescent Treponemal Antibody Absorption Immunoglobulin G Assay for Syphilis Testing, Journal of Clinical Microbiology, Oct. 1999, pp. 3233-3234, vol. 37, No. 10.
Koga et al., A chip-based miniaturized format for protein-expression profiling: The exploitation of comprehensively produced antibodies, Electrophoresis, 2006, pp. 3676-3683, vol. 27.

(Continued)

Primary Examiner — Chris L Chin
(74) Attorney, Agent, or Firm — Clayton, Howarth & Cannon, P.C.

(57) ABSTRACT

The present invention discloses using SPR technology to detect MM related genomic imbalances in bone marrow samples. An efficient formula to make a mixed SAM that can greatly enhance the immobilization ability of the metal surface in SPR based techniques, which is good for the immobilization of DNA markers used for the identification of MM related genomic imbalances in bone marrow samples is also disclosed.

14 Claims, No Drawings

OTHER PUBLICATIONS

Lee, J. et al., Characterization of a self-assembled monolayer of thiol on a gold surface and the fabrication of a biosensor chip based on surface plasmon resonance for detecting anti-GAD antibody, Biosensors and Bioelectronics, 2005, pp. 1422-1427, vol. 20.

Lee, W. et al., Fabrication of self-assembled protein a monolayer and its application as an immunosensor, Biosensors and Bioelectronics, 2003, pp. 185-192, vol. 19.

Löfäs, Dextran modified self-assembled monolayer surfaces for use in biointeraction analysis with surface plasmon resonance, Pure & Applied Chem., 1995, pp. 829-834, vol. 67, No. 5.

McGill et al., Analysis of the binding of monoclonal and polyclonal antibodies to the glycoproteins of antigenic variants of human respiratory syncytial virus by surface plasmon resonance, Journal of Immunological Methods, 2005, pp. 143-152, vol. 297.

Metzger et al., Biosensor Analysis of $2-Glycoprotein I-Reactive Autoantibodies: Evidence for Isotype-Specific Binding and Differentiation of Pathogenic from Infection-Induced Antibodies, Clinical Chemistry, 2007, pp. 11347-1143, vol. 53, No. 6.

Mullet et al., "Surface Plasmon Resonance-Based Immunoassays," Methods, 2000, pp. 77-91, vol. 22.

Nanoprobes E-News, "Gold Particles for Surface Plasmon Resonance Detection," 2004, p. 5, para. 1-3, vol. 5, No. 6.

Soroka et al., "Modification of Rapid Human Immunodeficiency Virus (HIV) Anitbody Assay Protocols for Detecting Recent HIV Seroconversion," Clinical and Diagnostic Laboratory Immunology, Aug. 2005, pp. 918-921, vol. 12, No. 8.

Stock et al., "Migration of human melanoma cells depends on extracellular pH and Na+/H+ exchange," J Physiol, 2005, pp. 225-238, vol. 567.1.

Subramanian et al., "A mixed self-assembled monolayer-based surface plasmon immunosensor for detection of E. coli O157:H7," Biosensors and Bioelectronics, 2006, pp. 998-1006, vol. 21.

Tong et al., "Diagnostic developments involving cell-free (circulating) nucleic acids," Clinica Chimica Acta, 2006, pp. 187-196, vol. 363.

Urban et al., "Receptor recognition by a hepatitis B virus reveals a novel mode of high affinity virus-receptor interaction," The EMBO Journal, 2000, pp. 1217-1227, vol. 19, No. 6.

Wang et al., "A new approach for the detection of DNA sequences in amplified nucleic acids by a surface plasmon resonance biosensor," Biosensors and Bioelectronics, 2004, pp. 598-605, vol. 20.

Wu et al., "Study of MMLV RT—Binding with DNA using Surface Plasmon Resonance Biosensor," Acta Biochimica et Biophysica Sinica, 2005, pp. 634-642, vol. 37, No. 9.

METHOD OF SURFACE PLASMON RESONANCE (SPR) TO DETECT GENOMIC ABERRATIONS IN PATIENTS WITH MULTIPLE MYELOMA

CROSS-REFERENCE TO RELATED APPLICATIONS

This application claims priority benefits under 35 U.S.C. 365(a) of International Application No. PCT/US07/76658, filed 23 Aug. 2007, which claims priority under the Paris Convention to U.S. Provisional Patent Application No. 60/826,859, filed on 25 Sep. 2006, which applications are incorporated by reference herein in their entireties, including but not limited to those portions that specifically appear hereinafter.

TECHNICAL FIELD

The present invention relates to a method of using SPR technology to simultaneously detect genomic aberrations in patients with multiple myeloma.

INDUSTRIAL APPLICABILITY

It has been recognized that it would be advantageous to develop a label-free and high-throughput technique to simultaneously detect genomic imbalances in patients with multiple myeloma. SPR technology has the characteristics of providing unlabeled, high-throughput, and on-line parallel analysis. The METHOD OF SURFACE PLASMON RESONANCE (SPR) TECHNOLOGY TO DETECT GENOMIC ABERRATIONS IN PATIENTS WITH MULTIPLE MYELOMA provides a method of using SPR technology to simultaneously detect genomic imbalances in patients with multiple myeloma (MM).

METHOD OF SURFACE PLASMON RESONANCE (SPR) TECHNOLOGY TO DETECT GENOMIC ABERRATIONS IN PATIENTS WITH MULTIPLE MYELOMA relates to a novel method of using SPR technology in detecting genomic disorders, which is significant for the management of patients with MM. METHOD OF SURFACE PLASMON RESONANCE (SPR) TECHNOLOGY TO DETECT GENOMIC ABERRATIONS IN PATIENTS WITH MULTIPLE MYELOMA provides an efficient formula to make a mixed SAM in and a method of using thereof for the immobilization of relevant genomic markers in an SPR system for detecting genomic imbalances in patients with multiple myeloma.

DISCLOSURE OF THE INVENTION

Surface plasmon resonance (SPR) technology has been employed for quantitative and qualitative analysis in analytical chemistry, biochemistry, physics and engineering. SPR technology has become a leading technology in the field of direct real-time observation of biomolecular interactions.

SPR technology is highly sensitive to changes that occur at the interface between a metal and a dielectric medium (e.g., water, air, etc). In general, a high-throughput SPR instrument consists of an auto-sampling robot, a high resolution CCD (charge-coupled device) camera, and gold or silver-coated glass slide chips each with more than 4 array cells embedded in a plastic support platform.

SPR technology exploits surface plasmons (special electromagnetic waves) that can be excited at certain metal interfaces, most notably silver and gold. When incident light is coupled with the metal interface at angles greater than the critical angle, the reflected light exhibits a sharp attenuation (SPR minimum) in reflectivity owing to the resonant transfer of energy from the incident light to a surface plasmon. The incident angle (or wavelength) at which the resonance occurs is highly dependent upon the refractive index in the immediate vicinity of the metal surface. Binding of biomolecules at the surface changes the local refractive index and results in a shift of the SPR minimum. By monitoring changes in the SPR signal, it is possible to measure binding activities at the surface in real time. Traditional SPR spectroscopy sensors, which measure the entire SPR curve as a function of angle or wavelength, have been widely used, but offer limited throughput. The high-throughput capability of a high-throughput SPR instrument is largely due to its imaging system. The development of SPR imaging allows for the simultaneous measurement of thousands of biomolecule interactions.

Typically, a SPR imaging apparatus consists of a coherent p-polarized light source expanded with a beam expander and consequently reflected from a SPR active medium to a detector. A CCD camera collects the reflected light intensity in an image. SPR imaging measurements are performed at a fixed angle of incidence that falls within a linear region of the SPR dip; changes in light intensity are proportional to the changes in the refractive index caused by binding of biomolecules to the surface. As a result, gray-level intensity correlates with the amount of material bound to the sensing region. In addition, one of the factors determining the sensitivity of a SPR imaging system is the intensity of the light source. The signal strength from the metal surface is linearly proportional to the incoming light strength, so a laser light source is preferred over light-emitting diode and halogen lamps.

The SPR instrument is an optical biosensor that measures binding events of biomolecules at a metal surface by detecting changes in the local refractive index. The depth probed at the metal-aqueous interface is typically 200 nm, making SPR a surface-sensitive technique ideal for studying interactions between immobilized biomolecules and a solution-phase analyte. SPR technology offers several advantages over conventional techniques, such as fluorescence or ELISA (enzyme-linked immunosorbent assay) based approaches. First, because SPR measurements are based on refractive index changes, detection of an analyte is label free and direct. The analyte does not require any special characteristics or labels (radioactive or fluorescent) and can be detected directly, without the need for multistep detection protocols. Secondly, the measurements can be performed in real time, allowing the user to collect kinetic data, as well as thermodynamic data. Lastly, SPR is a versatile technique, capable of detecting analyte over a wide range of molecular weights and binding affinities. Therefore, SPR technology is a powerful tool for studying biomolecule interactions. So far, in research settings, SPR based techniques have been used to investigate protein-peptide interactions, cellular ligation, protein-DNA interactions, and DNA hybridization. However, SPR based approaches have not yet been explored in clinical medicine, especially in clinical laboratory medicine.

The present invention relates to the application of SPR technology in medical diagnostics, i.e., detection of genomic aberrations for patients with multiple myeloma (MM).

MM is the prototypic monoclonal B-cell neoplasm that is derived from the autonomous proliferation of plasma cells and associated with paraprotein production and osteolytic bone lesions. MM primarily affects middle-aged to elderly patients. Blacks and males are affected more often than whites and females. MM has remained an incurable disease, and effective therapeutic approaches are urgently required to patients with MM at different risk groups. Standard prognostic factors include serum $\beta_2$-microglobulin, C-reactive protein (CRP), bone marrow plasma cell morphology, and plasma cell proliferation (plasma cell labeling index). These factors are independently associated with prognosis of patients with MM. There is considerable interest in characterizing genomic markers to establish prognostic models that allow a better estimation of an individual patient's prognosis.

Fluorescence in-situ hybridization (FISH) allows detection of chromosomal aberrations in both actively dividing cells and interphase nuclei. Recently, the cytoplasm immunoglobulin (Ig) enhanced interphase FISH has been used to detect the most common genomic abnormalities in patients with MM, including deletions of 13q14 and 17q13.1 as well as 14q32 translocations. Importantly, three distinct prognostic groups have been identified including those with a median survival time of 24.7 months (the t(4; 14) and/or t(14; 16), and/or 17p13.1 deletion), 42.3 months (13q14 deletions without the t(4; 14), t(14; 16), or 17p13.1 deletion), and 50.5 months (only the t(11; 14) or none of the abnormalities tested) in the patients treated with conventional chemotherapy.

Unfortunately, the FISH analyses reported are too cumbersome for routine clinical use in most laboratories. In addition, FISH requires fluorescent labels, and cannot identify different genomic aberrations simultaneously. Recently, genomic array (or called array CGH) has been reported as a reliable approach for the detection of genomic disorders. However, genomic array has to utilize fluorescent labels for detection. SPR technology has the ability of providing unlabel, high-throughput, and on-line parallel analysis, and has been demonstrated by us to serve as a powerful tool in detecting genomic aberrations for patients with MM.

REFERENCES (1) Wang R, Minunni M, Tombelli S, Mascini M. A new approach for the detection of DNA sequences in amplified nucleic acids by a surface plasmon resonance biosensor. Biosens Bioelectron. 2004 Oct. 15; 20(3):598-605
(2) Langmuir and Langmuir-Blodgett Films. INSTRUMENTS LTD, Application Note #107
(3) Mullett W M, Lai E P, Yeung J M. Surface plasmon resonance-based immunoassays. Methods. 2000 September; 22(1):77-91.
(4) Takuo A., Kazunori I., et al. A surface plasmon resonance probe with a novel integrated reference sensor surface. Biosens Bioelectron. 2003 Oct. 15; 18(12):1447-53
(5) Sato Y, Sato K, Hosokawa K, Maeda M. Surface plasmon resonance imaging on a microchip for detection of DNA-modified gold nanoparticles deposited onto the surface in a non-cross-linking configuration. Anal Biochem. 2006 Aug. 1; 355(1):125-31. Epub 2006 May 19.
(6) Spadavecchia J, Manera M G, Quaranta F, Siciliano P, Rella R. Surface plamon resonance imaging of DNA based biosensors for potential applications in food analysis. Biosens Bioelectron. 2005 Dec. 15; 21(6):894-900.
(7) Yao X, Li X, Toledo F, Zurita-Lopez C, Gutova M, Momand J, Zhou F. Sub-attomole oligonucleotide and p53 cDNA determinations via a high-resolution surface plasmon resonance combined with oligonucleotide-capped gold nanoparticle signal amplification. Anal Biochem. 2006 Jul. 15; 354(2):220-8. Epub 2006 May 6.
(8) Okumura A, Sato Y, Kyo M, Kawaguchi H. Point mutation detection with the sandwich method employing hydrogel nanospheres by the surface plasmon resonance imaging technique. Anal Biochem. 2005
(9) Sandberg A A, Chen Z: FISH Analysis. In: Methods in Molecular Medicine, Vol. 55: Hematologic Malignancies: Methods and Techniques. Faguet G B, eds. Humana Press, Inc., 2000
(10) Kaufmann H, Urbauer E, Ackermann J, Huber H, Drach J. Advances in the biology and therapeutic management of multiple myeloma. *Ann Hematol* 2001; 80(8):445-51.
(11) Fonseca R, Barlogie B, Bataille R, Bastard C, Bergsagel P L, Chesi M, Davies F E, Drach J, Greipp P R, Kirsch I R, Kuehl W M, Hernandez J M, Minvielle S, Pilarski L M, Shaughnessy J D, Jr., Stewart A K, Avet-Loiseau H. Genetics and cytogenetics of multiple myeloma: a workshop report. *Cancer Res* 2004; 64(4):1546-58.
(12) Fonseca R, Blood E, Rue M, Harrington D, Oken M M, Kyle R A, Dewald G W, Van Ness B, Van Wier S A, Henderson K J, Bailey R J, Greipp P R. Clinical and biologic implications of recurrent genomic aberrations in myeloma. *Blood* 2003; 101(11):4569-75.

MODES FOR CARRYING OUT THE INVENTION

Before the present method of using SPR technology to qualitatively detect the presence of specific genomic imbalances in patients with MM is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference "a DNA marker" includes reference to two or more such DNA markers.

In describing and claiming the present invention, the following terminology will be used in accordance with the definitions set out below.

"Proteins" and "peptides" are well-known terms in the art, and are not precisely defined in the art in terms of the number of amino acids that each includes. As used herein, these terms are given their ordinary meaning in the art. Generally, peptides are amino acid sequences of less than about 100 amino acids in length, but can include sequences of up to 300 amino acids. Proteins generally are considered to be molecules of at least 100 amino acids.

As used herein, a "metal binding tag" refers to a group of molecules that can become fastened to a metal that is coordinated by a chelate. Suitable groups of such molecules include amino acid sequences including, but not limited to, histidines and cysteines ("polyamino acid tags"). Metal binding tags include histidine tags, defined below.

"Signaling entity" means an entity that is capable of indicating its existence in a particular sample or at a particular location. Signaling entities of the invention can be those that are identifiable by the unaided human eye, those that may be invisible in isolation but may be detectable by the unaided human eye if in sufficient quantity (e.g., colloid particles), entities that absorb or emit electromagnetic radiation at a level or within a wavelength range such that they can be readily determined visibly (unaided or with a microscope including an electron microscope or the like), or spectroscopically, entities that can be determined electronically or electrochemically, such as redox-active molecules exhibiting a characteristic oxidation/reduction pattern upon exposure to appropriate activation energy ("electronic signaling entities"), or the like. Examples include dyes, pigments, electroactive molecules such as redox-active molecules, fluorescent moieties (including, by definition, phosphorescent moieties), up-regulating phosphors, chemiluminescent entities, electrochemiluminescent entities, or enzyme-linked signaling moieties including horse radish peroxidase and alkaline phosphatase.

"Precursors of signaling entities" are entities that by themselves may not have signaling capability but, upon chemical, electrochemical, electrical, magnetic, or physical interaction with another species, become signaling entities. An example includes a chromophore having the ability to emit radiation within a particular, detectable wavelength only upon chemical interaction with another molecule. Precursors of signaling entities are distinguishable from, but are included within the definition of, "signaling entities" as used herein.

As used herein, "fastened to or adapted to be fastened", in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "fastened" in this context includes multiple chemical linkages, multiple chemical/biological linkages, etc., including, but not limited to, a binding species such as a peptide synthesized on a polystyrene bead, a binding species specifically biologically coupled to an antibody which is bound to a protein such as protein A, which is covalently attached to a bead, a binding species that forms a part (via genetic engineering) of a molecule such as GST or Phage, which in turn is specifically biologically bound to a binding partner covalently fastened to a surface (e.g., glutathione in the case of GST), etc. As another example, a moiety covalently linked to a thiol is adapted to be fastened to a gold surface since thiols bind gold covalently. Similarly, a species carrying a metal binding tag is adapted to be fastened to a surface that carries a molecule covalently attached to the surface (such as thiol/gold binding) and which molecule also presents a chelate coordinating a metal. A species also is adapted to be fastened to a surface if that surface carries a particular nucleotide sequence, and the species includes a complementary nucleotide sequence.

"Covalently fastened" means fastened via nothing other than by one or more covalent bonds. E.g. a species that is covalently coupled, via EDC/NHS chemistry, to a carboxylate-presenting alkyl thiol which is in turn fastened to a gold surface, is covalently fastened to that surface.

"Specifically fastened (or bound)" or "adapted to be specifically fastened (or bound)" means a species is chemically or biochemically linked to another specimen or to a surface as described above with respect to the definition of "fastened to or adapted to be fastened", but excluding all non-specific binding.

"Non-specific binding", as used herein, is given its ordinary meaning in the field of biochemistry.

As used herein, a component that is "immobilized relative to" another component either is fastened to the other component or is indirectly fastened to the other component, e.g., by being fastened to a third component to which the other component also is fastened, or otherwise is translationally associated with the other component. For example, a signaling entity is immobilized with respect to a binding species if the signaling entity is fastened to the binding species, is fastened to a colloid particle to which the binding species is fastened, is fastened to a dendrimer or polymer to which the binding species is fastened, etc. A colloid particle is immobilized relative to another colloid particle if a species fastened to the surface of the first colloid particle attaches to an entity, and a species on the surface of the second colloid particle attaches to the same entity, where the entity can be a single entity, a complex entity of multiple species, a cell, another particle, etc.

The term "sample" refers to any medium suspected of containing an analyte, such as a binding partner, the presence or quantity of which is desirably determined. The sample can be a biological sample such as a cell, cell lysate, tissue, serum, blood or other fluid from a biological source, a biochemical sample such as products from a cDNA library, an environmental sample such as a soil extract, or any other medium, biological or non-biological, including synthetic material, that can advantageously be evaluated in accordance with the invention.

A "sample suspected of containing" a particular component means a sample with respect to which the content of the component is unknown. The sample may be unknown to contain the particular component, or may be known to contain the particular component but in an unknown quantity.

As used herein, a "metal binding tag" refers to a group of molecules that can become fastened to a metal that is coordinated by a chelate. Suitable groups of such molecules include amino acid sequences, typically from about 2 to about 10 amino acid residues. These include, but are not limited to, histidines and cysteines ("polyamino acid tags"). Such binding tags, when they include histidine, can be referred to as a "poly-histidine tract" or "histidine tag" or "HIS-tag", and can be present at either the amino- or carboxy-terminus, or at any exposed region of a peptide or protein or nucleic acid. A poly-histidine tract of six to ten residues is preferred for use in the invention. The poly-histidine tract is also defined functionally as being the number of consecutive histidine residues added to a protein of interest which allows for the affinity purification of the resulting protein on a metal chelate column, or the identification of a protein terminus through interaction with another molecule (e.g. an antibody reactive with the HIS-tag).

A "moiety that can coordinate a metal", as used herein, means any molecule that can occupy at least two coordination sites on a metal atom, such as a metal binding tag or a chelate.

"Affinity tag" is given its ordinary meaning in the art. Affinity tags include, for example, metal binding tags, GST (in GST/glutathione binding clip), and streptavidin (in biotin/streptavidin binding). At various locations herein specific affinity tags are described in connection with binding interactions. It is to be understood that the invention involves, in any embodiment employing an affinity tag, a series of individual embodiments each involving selection of any of the affinity tags described herein.

The term "self-assembled monolayer" (SAM) refers to a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. See Laibinis. P. E.; Hickman. J.: Wrighton. M. S.: Whitesides, G. M. Science 245, 845 (1989). Bain. C.; Evall. J.: Whitesides. G. M. J. Am. Chem. Soc. 111, 7155-7164 (1989), Bain, C.; Whitesides, G. M. J. Am. Chem. Soc. 111, 7164-7175 (1989), each of which is incorporated herein by reference. The SAM can be made up completely of SAM-forming species that form close-packed SAMs at surfaces, or these species in combination with molecular wires or other species able to promote electronic communication through the SAM (including defect-promoting species able to participate in a SAM), or other species able to participate in a SAM, and any combination of these. Preferably, all of the species that participate in the SAM include a functionality that binds, optionally covalently, to the surface, such as a thiol which will bind covalently to a gold surface. A self-assembled monolayer on a surface, in accordance with the invention, can be comprised of a mixture of species (e.g. thiol species when gold is the surface) that can present (expose) essentially any chemical or biological functionality. For example, they can include tri-ethylene glycol-terminated species (e.g. tri-ethylene glycol-terminated thiols) to resist non-specific adsorption, and other species (e.g. thiols) terminating in a binding partner of an affinity tag, e.g. terminating in a chelate that can coordinate a metal such as nitrilotriacetic acid which, when in complex with nickel atoms, captures a metal binding tagged-species such as a histidine-tagged binding species.

"Molecular wires" as used herein, means wires that enhance the ability of a fluid encountering a SAM-coated electrode to communicate electrically with the electrode. This includes conductive molecules or, as mentioned above and exemplified more fully below, molecules that can cause defects in the SAM allowing communication with the electrode. A non-limiting list of additional molecular wires includes 2-mercaptopyridine, 2-mercaptobenzothiazole, dithiothreitol, 1,2-benzenedithiol, 1,2-benzene-dimethanethiol, benzene-ethanethiol, and 2-mercaptoethyl-ether. Conductivity of a monolayer can also be enhanced by the addition of molecules that promote conductivity in the plane of the electrode. Conducting SAMs can be composed of, but are not limited to: 1) poly (ethynylphenyl) chains terminated with a sulfur; 2) an alkyl thiol terminated with a benzene ring; 3) an alkyl thiol terminated with a DNA base; 4) any sulfur terminated species that packs poorly into a monolayer; 5) all of the above plus or minus alkyl thiol spacer molecules terminated with either ethylene glycol units or methyl groups to inhibit non specific adsorption. Thiols are described because of their affinity for gold in ready formation of a SAM. Other molecules can be substituted for thiols as known in the art from U.S. Pat. No. 5,620,820, and other references. Molecular wires typically, because of their bulk or other conformation, create defects in an otherwise relatively tightly-packed SAM to prevent the SAM from tightly sealing the surface against fluids to which it is exposed. The molecular wire causes disruption of the tightly-packed self-assembled structure, thereby defining defects that allow fluid to which the surface is exposed to communicate electrically with the surface. In this context, the fluid communicates electrically with the surface by contacting the surface or coming in close enough proximity to the surface that electronic communication via tunneling or the like can occur.

The term "biological binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

The term "binding" or "bound" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

The term "binding partner" refers to a molecule that can undergo binding with a particular molecule. Biological binding partners are examples. For example, Protein A is a binding partner of the biological molecule IgG, and vice versa.

The term "determining" refers to quantitative or qualitative analysis of a species via, for example, spectroscopy, ellipsometry, piezoelectric measurement, immunoassay, electrochemical measurement, and the like. "Determining" also means detecting or quantifying interaction between species, e.g. detection of binding between two species.

The term "self-assembled mixed monolayer" refers to a heterogeneous self-assembled monolayer, that is, one made up of a relatively ordered assembly of at least two different molecules.

"Synthetic molecule", means a molecule that is not naturally occurring, rather, one synthesized under the direction of human or human-created or human-directed control.

The present invention generally relates to a method of using SPR technology to detect specific DNA markers significantly associated with MM. More specifically, the present invention relates to using SPR technology to qualitatively detect the presence of specific genomic imbalances (DNA markers) associated with MM in a bone marrow sample. In addition, the present invention provides an efficient formula to make a mixed SAM that can greatly enhance the immobilization ability of the metal surface, which is desirable for the immobilization of relevant DNA markers for detection. For the detection of MM in bone marrow, DNA markers suitable for the present invention, can be DNA markers (e.g., in BAC clones) specific for the loci of p53 and 13q14 as well as chromosomes 5, 9, and 15, etc. These DNA markers are significantly associated with MM.

To enhance the sensitivity and specificity of the SPR technology, a linking layer is attached onto the gold film on the surface of a glass chip that serves as a functional structure for further modification of the gold film surface. So far, several immobilization chemistries are suitable for the formation of the linking layer, including alkanethiols, hydrogel, silanes, polymer films and polypeptides. Moreover, there are several methods to attach the linking layer onto the thin gold surface, such as the Langmuir-Blodgett film method and the self-assembled monolayer (SAM) approach.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

Example 1

Detection of MM-Related DNA Markers in Bone Marrow

Testing sample: bone marrow (1-2 ml)

1) Genomic markers represented: DNA markers (e.g., in BAC clones) specific for the loci of p53 and 13q14 as well as chromosomes 5, 9, and 15, etc. These DNA markers are significantly associated with MM.

2) Procedure:

a) Formation of a Link Layer on the Surface of a Gold-Film Glass Chip:

In order to enhance the analytic sensitivity and specificity of SPR technology a link layer is attached onto the gold film on the surface of a glass chip to serve as a functional structure for further modification of the gold film surface. So far, several immobilization chemistries are suitable for the formation of the link layer, including alkanethiols, hydrogel, silanes, polymer films and polypeptides. Moreover, there are several methods to attach the link layer onto the thin gold surface, such as Langmuir-Blodgett film method and self-assembled monolayer (SAM) approach.

In this example, alkanethiols are chosen to form a mixed SAM on the surface of a gold film because a mixed SAM of long-chain alkanethiols can bind with biomolecules through their suitable reactive groups (such as carboxyl-terminal) on one side and react with the gold film through a gold-complexing thiol on the other side. In detail, ten millimolar mixed solutions consisting of 10:1 molar ratios of 3-mercaptopropanol (3-MPOH) to 11-mercaptoundecanoic acid (11-MUA) are prepared in pure ethanol. The prepared gold films are immersed in the solutions for 24 h and then are rinsed several times with ethanol and deionized water. After rinsing, the gold films are dried in a pure $N_2$ gas stream.

By comparing different alkanethiols, an efficient formula is generated, i.e., ten millimolar mixed solutions consisting of 10:1 molar ratios of 3-mercaptopropanol (3-MPOH) to 11-mercaptoundecanoic acid (11-MUA), from which to make a mixed SAM that is good for the immobilization of relevant DNA markers.

b) Immobilization of Genomic Markers on the Surface of the Link Layer

To improve the orientation of the captured biomolecules and to reduce non-specific binding, the biotin-streptavidin system is employed in this invention. First, we either biotinylate the carboxyl-terminated groups of a SAM with subsequent binding of streptavidin, or immobilize streptavidin directly to the SAM, dependingon the molecular weight of detected molecules. In detail, the flow rates of all solutions are maintained at 5 µl/min during immobilization. The link-layer/gold-film glass chips as prepared above are rinsed in 0.1M MES buffer (pH 4.7-5.5). Afterwards, they are soaked in a clean bottle containing 5 ml of 0.1M MES buffer (2-morpholinoethane sulfonic acid) with the gold-coated layers facing upward. The carboxyl groups are activated by adding 65 µl of 100 mg/ml EDC(N-ethyl-N_-(3-diethylaminopropyl) carbodiimide), and then conjugated with 130 µl of biotin hydrazide (50 mM). After 12 h at room temperature with gentle shaking, the chips are cleaned several times with ultrapure water and HBS buffer (pH 7.0). Finally, the chips are cleaned and dried under a pure $N_2$ gas stream. Then streptavidin is immobilized by injecting streptavidin (20 µg/ml in HBS buffer pH 7.4) for 7 min.

To immobilize streptavidin directly to a SAM, the SAM surface is first equilibrated with HBS buffer for about 30 min to obtain a stable baseline. After obtaining a stable baseline, terminal carboxylic groups of the mixed SAM are activated with a 7 min pulse of a 1:1 mixture of 0.1M NHS and 0.1M EDC, and then streptavidin (200 µg/ml) in 10 mM sodium acetate buffer at pH 5.5 is injected for 15 min. After immobilization of the streptavidin, 1.0Methanolamine-HCl is flowed over the SAM surface for 10 min to block the remaining active sites, which is also effective for blocking non-specific binding. Secondly, the DNA markers represented are biotinylated by using a nick translation technique according to the standard protocol.

Measuring the level of biotin incorporation is carried out with a EZ-link sulfo-NHS-LCBiotinylation Kit according to the manufacturer's protocol. Afterwards, the biotinylated DNA markers are denatured at 98° C. for about 5 min, and then quickly cooled in ice to make the markers being single stranded. Lastly, the single-strand and biotinylated DNA markers covalently bind to the streptavidin attached to the SAM. Briefly, the biotinylated DNA markers each at about 1-2 ng/ul in TE buffer are injected into each array cell, respectively, for 7 min. The unbound biotinylated DNA markers are washed away by using a mixed solution of 25 mM NaOH/ 0.2M NaCl for 2 min.

Testing a Sample

Based on the standard protocol, DNA is extracted from bone marrow. The normal control DNA is obtained from healthy human beings and biotinylated with the nick translation technique according to the standard protocol. Then, the same amount of sample DNA (about 1 ug) and control DNA (about 1 ug) combed with a 50 times higher amount of human Cot-1 DNA are mixed together and denatured at 100° C. for about 5 min, then placed in an ice slurry for 5 min. Subsequently, the denatured mixture with 45 µl of Hybridization Buffer (e.g., 5.5 ml formamide, lg Dextran sulfate, 0.5 ml 20×SSC, and 1 ml water in a total volume of 7 mL) is added onto the surface of the link-layer/gold-film glass chip markers at 37° C. overnight in a shaker in order to hybridize with the immobilized DNA markers. After washing out unhybrdized sample/control DNA with three washing solutions (50% formamide, 10% 20×SSC, 40% distilled water; 4×SSC/0.05% Tween 20; 4×SSC), the hybridized link-layer/gold-film glass chip is analyzed with SPR technology according to the standard operation protocol.

For comparison purposes, standard fluorescence in situ hybridization (FISH) analyses are also performed to verify the results obtained with SPR technology. By comparing different alkanethiols, an efficient formula is generated to make a mixed SAM that is good for the immobilization of MM related DNA markers.

The data show that using SPR technology can reliably detect biotinylated DNA markers (e.g., in BAC clones) specific for the loci of p53 and 13q14 as well as chromosomes 5, 9, and 15, etc. These DNA markers are significantly associated with the prognosis of MM.

In addition, the data also shows that in a qualitative assay, the presence of specific DNA loss or gain in a bone marrow sample coincides with those as identified by standard FISH technique, which can be used for the diagnosis of genomic aberrations in patients with MM.

The following is a more detailed description of the procedure for chip preparation and probe preparation:

The probes can be prepared from BAC clones or synthesized and be labeled by —SH, biotin so that the probes can form monolayer on the bare gold chip surface or bind on the modified chip surface. The probes from BAC clones can be labeled by random PCR or nick translation to introduce the —SH or biotin into the probes. The probes should be denatured to single stands prior to use. If oligonucleotide probes (20-60 bp) are used, the probes can be synthesized and the —SH or biotin can be added to the probe terminus. Once the probes are denatured to single strands, the probes can be immobilizes on the chip surface.

Immobilization of thiol-labeled probes on the bare gold chip surface: the gold sensor chip was cleaned with a solution consisting of $H_2O_2$ (30%), NH3 (30%) and milliQ water in a 1:1:5 ratio for 10 min and then thoroughly washed with milliQ water. After the cleaning step, the sensor chip was covered with a solution (1 uM, 1 ml) of thiolated probes in immobilization solution ($KH_2PO_4$ 1M, pH 3.8) and incubated at room temperature for 2 h. Afterwards, the sensor chip was washed with milliQ water and treated with 1 mM (1 ml) blocking thiol solution (MCH, 1 uM) at room temperature for one hour in dark. After washing with water, it was left to dry to be mounted onto the plastic support and docked into the SPR instrument ready for hybridization reactions.

Immobilization of oligonucleotide probes labeled with biotin on the modified chip surface: immobilization of the oligonucleotide probes labeled with biotin can use the streptavidin-biotin method.

The dextran-modified chips were made with the following description:

Cleanliness of Substrate

Metal substrates (copper, silver, aluminum or gold) were cleaned with strong oxidizing chemicals ("piranha" solution-$H_2SO_4:H_2O_2$) or argon plasmas, and their surfaces were washed with ultra pure water and degassed ethanol. After rinsing, the substrates were dried with pure $N_2$ gas stream.

Preparation of Self-Assembled Monolayers

Single-component or mixed self-assembled monolayers (SAMs) of organosulfur compounds (thiols, disulfides, sulfides) on the clean metal substrate have been widely applied for chemical modification to develop chemical and biological sensor chips. Preparing SAMs on metal substrates was achieved by immersion of a clean substrate into a dilute (~1-10 m M) ethanolic solution of organosulfur compounds for 12-18 h at room temperature.

Monolayers comprising a well-defined mixture of molecular structures are called "mixed" SAMs. There are three easy methods for synthesizing mixed SAMs: (1) coadsorption from solutions containing mixtures of alkanethiols ($HS(CH_2)_nR+HS(CH_2)_nR'$), (2) adsorption of asymmetric dialkyl disulfides ($R(CH_2)_mS—S(CH_2)_mR'$), and (3) adsorption of asymmetric dialkylsulfides ($R(CH_2)_mS(CH_2)_nR'$), where n and m are the number of methylene units (range from 3 to 21) and R represents the end group of the alkyl chain (—$CH_3$, —OH, —COOH, $NH_2$) active for covalently binding ligands or biocompatible substance. Mixed SAMs are useful for decreasing the steric hindrance of interfacial reaction that, in turn, is useful for studying the properties and biology of cells.

Rather than using single-component for preparing the SAM in conventional methods, "mixed" SAMs were used in the present invention, which provides various functional groups and branching structures to decrease the steric hindrance of interfacial reaction that, in turn, is useful for studying the biomolecular interaction analysis.

Methods for modifying SAMs after their formation are critical for the development of surfaces that present the large, complex ligands and molecules needed for biology and biochemistry. There are two important techniques for modifying SAMs:

(1) Direct reaction with exposed functional groups: under appropriate reaction conditions, terminal functional groups (—OH, —COOH) exposed on the surface of a SAM immersed in a solution of ligands could react directly with the molecules present in solution. Many direct immobilization techniques have been adapted from methods for immobilizing DNA, polypeptides, and proteins on SAMs (2) Activation of surfaces for reactions: an operationally different approach to the functionalization of the surfaces of SAMs is to form a reactive intermediate, which is then coupled to a ligand. In this invention, we chose epoxy activation method to couple polysaccharide or a swellable organic polymer. In detail, 2-(2-Aminoethoxy)ethanol (AEE) was coupled to carboxyl-functionalized SAM using peptide coupling reagents (N-hydroxysuccinimide/N-Ethyl-N'-(3-dimethylaminopropyl)-carbodiimide (EDC/NHS)), and the terminal hydroxyl groups were further reacted with epichlorohydrin to produce epoxy-functionalized surfaces. These were subsequently reacted with hydroxyl moieties of polysaccharide or organic polymer. Subsequently, the polysaccharide chains were carboxylated through treatment with bromoacetic acid more than one time. The resultant material offered for further functionalization with biomolecules.

Streptavidin Immobilized on the Dextran-Modified Chip Surface 35 ul of a solution containing 50 mM NHS and 200 mM EDAC in water were injected to activate the dextran-modified surface. The chip was further modified with streptavidin (200 ug/ml in acetate buffer 10 mM, pH5.0). Then, the residual reacting sites were blocked with 35 ul solution of ethanolamine hydrochloride (pH 8.6, 1M water solution). Finally, the biotinylated predenatured probe was added (100 ul probe, 1 uM in immobilization buffer (NaCl 300 mM, $Na_2HPO_4$ 20 mM, EDTA 0.1 mM, pH 7.4).

Sample DNA Preparation

The DNA can be extracted by using commercial extraction kits. If necessary, the DNA can be further amplified by using methods, such as conventional PCR, RT-PCR, nested-PCR, DOP-PCR, random-PCR, etc.

Sample DNA Denaturing and Blocking

Prior to SPR testing, sample DNA needs to be pre-treated to become single-stranded available for hybridization to the immobilized probe. If needed, the DNA may be treated by supersonic or endonuclease The high temperature denaturing method was employed. This method was found to be a simple and useful way to obtain single-stranded DNA available for hybridization. The principle of this method relies on the use of small (20 bases) oligonucleotides added to the denaturation mixture. These oligonucleotides are complementary to some sequences on the strand that hybridizes to the immobilized probe. By the interaction between the thermally separated DNA strands and these oligonucleotides, surface hybridization can occur. The whole denaturation procedure was combined with sense and antisense primers. The protocol was composed by a 5 min incubation step at 95° C. and then 1 min at 50° C., suitable for primers annealing in the PCR procedure. Cotl DNA, salmon sperm DNA or yeast tRNA etc. were added into the denaturation system to block the chip so that the background and the nonspecific hybridization could be minimized.

Hybridization

Hybridization experiments were conducted in the SPR instrument at a flow rate of 5 ul/min (at 25° C.) injecting 25 ul of the sample DNA as blocked by cot I DNA on the probe immobilized chip. The reaction was monitored for 5 min and then the sensor chip was automatically washed with hybridization buffer to remove the unbound DNA material. The analytical signal, reported as resonance units (RU), was derived from the difference between the final value and the value recorded before the target injection (baseline). It is referred as on-line hybridization method. The hybridization experiments can also be conducted off the SPR instrument, which is referred as off-line hybridization method. Advantage of the off-line hybridization method is that temperature and time can be controlled easily for the experiments.

Results Interpretation

A significant number of samples (e.g. 20-30) need to be done in order to establish a threshold for each DNA probe or marker. If the RU of a patient is greater than the value of Mean+3SD of the threshold, the patient will be considered abnormal for the marker tested It is to be understood that the above-described embodiments are only illustrative of application of the principles of the present invention. Numerous modifications and alternative embodiments can be derived without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth in the claims.

What is claimed is:

1. A SPR biosensor chip for detecting the presence of MM related genomic imbalances in bone marrow samples prepared by forming a linking layer on the surface of a metal film on a glass chip and immobilizing of one or more DNA markers on the surface of the linking layer, wherein said metal film is treated with dextran using 2-(2-Aminoethoxy)ethanol (AEE) as a crosslinking agent and multiple bromoacetic acid reactions.

2. The SPR biosensor chip according to claim 1, wherein the linking layer is prepared by preparing a mixed SAM of long-chain alkanethiols which can bind with biomolecules through its suitable reactive groups on one side and react with said gold film through a gold-complexing thiol on the other side, modifying and activating the mixed SAMs.

3. The SPR biosensor chip according to claim 2, wherein said mixed SAMs is prepared by one of the following: (1) coadsorption from solutions containing mixtures of alkanethiols ($HS(CH_2)_nR+HS(CH_2)_nR'$), (2) adsorption of asymmetric dialkyl disulfides ($R(CH_2)_mS—S(CH_2)_nR'$), and (3) adsorption of asymmetric dialkylsulfides ($R(CH_2)_mS(CH_2)_nR'$), wherein n and m are the number of methylene units which is an integer from 3 to 21) and R represents the end group of the alkyl chain ($—CH_3$, $—OH$, $—COON$, $NH_2$) active for covalently binding ligands or biocompatible substance.

4. The SPR biosensor chip according to claim 2, wherein said modifying and activating the mixed SAMs is accomplished by an epoxy activation method to couple a polysaccharide or a swellable organic polymer comprising coupling 2-(2-Aminoethoxy)ethanol (AEE) to carboxyl-functionalized SAM using peptide coupling reagents (N-hydroxysuccinimide/N-Ethyl-N'-(3-dimethylaminopropyl)-carbodiimide (EDC/NHS)), and reacting with epichlorohydrin to produce epoxy-functionalized surfaces, which subsequently being reacted with hydroxyl moieties of the polysaccharide or organic polymer, the resulting polysaccharide chains are subsequently being carboxylated through treatment with bromoacetic acid multiple times.

5. The SPR biosensor chip according to claim 1, wherein said DNA marker is one or more members selected from a group consisting of BAC clones specific for the loci of p53, 13q14, chromosomes 5, 9, and 15, said DNA markers are significantly associated with MM.

6. The SPR biosensor chip according to claim 1, wherein said DNA marker is immobilized to the surface of the linking layer using a biotin-streptavidin system or —SH as the immobilization agent.

7. The SPR biosensor chip according to claim 1, wherein said metal is copper, silver, aluminum or gold.

8. A method for simultaneously detecting MM related genomic imbalances in bone marrow samples, comprising the steps of:
   1) preparing a surface plasmon resonance (SPR) system comprising:
      a) the SPR biosensor chip according to claim 1;
      b) a spectrophotometric means for receiving a first signal and a second signal from said biosensor surface, said second signal being received at a time after hybridization reaction of the sample to be tested and said DNA on said biosensor surface; and
      c) means for calculating and comparing properties of said first received signal and said second received signal to determine the presence of said DNA marker;
   2) preparing a DNA extract from a bone marrow sample to be tested and denaturing the DNA to produce a single stranded DNA preparation and contacting the resulting single stranded DNA preparation with said biosensor and spectrophotometrically receiving said first signal and said second signal; and
   3) calculating the differences between said received first and second signals to detect MM related genomic imbalances.

9. The method according to claim 8, wherein the linking layer is prepared by preparing a mixed SAM of long-chain alkanethiols which can bind with biomolecules through its suitable reactive groups on one side and react with said gold film through a gold-complexing thiol on the other side, modifying and activating the mixed SAMs.

10. The method according to claim 9, wherein said mixed SAMs is prepared by one of the following: (1) coadsorption from solutions containing mixtures of alkanethiols ($HS(CH_2)_nR+HS(CH_2)_nR'$), (2) adsorption of asymmetric dialkyl disulfides ($R(CH_2)_mS—S(CH_2)_nR'$), and (3) adsorption of asymmetric dialkylsulfides ($R(CH_2)_mS(CH_2)_nR'$), wherein n and m are the number of methylene units which is an integer from 3 to 21) and R represents the end group of the alkyl chain ($—CH_3$, $—OH$, $—COOH$, $NH_2$) active for covalently binding ligands or biocompatible substance.

11. The method according to claim 9, wherein said modifying and activating the mixed SAMs is accomplished by an epoxy activation method to couple a polysaccharide or a swellable organic polymer comprising coupling 2-(2-Aminoethoxy)ethanol (AEE) to carboxyl-functionalized SAM using peptide coupling reagents (N-hydroxysuccinimide/N-Ethyl-N'-(3-dimethylaminopropyl)-carbodiimide (EDC/NHS)), and reacting with epichlorohydrin to produce epoxy-functionalized surfaces, which subsequently being reacted with hydroxyl moieties of the polysaccharide or organic polymer, the resulting polysaccharide chains are subsequently being carboxylated through treatment with bromoacetic acid multiple times.

12. The method according to claim 8, wherein said DNA marker is one or more members selected from a group consisting of BAC clones specific for the loci of p53, 13q14, chromosomes 5, 9, and 15, said DNA markers are significantly associated with MM.

13. The method according to claim 8, wherein said DNA marker is immobilized to the surface of the linking layer using a biotin-streptavidin system or —SH as the immobilization agent.

14. The method according to claim 8, wherein said metal is copper, silver, aluminum or gold.

* * * * *